(12) United States Patent
Gill et al.

(10) Patent No.: US 10,751,513 B2
(45) Date of Patent: Aug. 25, 2020

(54) NEUROSURGICAL APPARATUS AND METHODS

(71) Applicant: RENISHAW PLC, Wotton-under-Edge, Gloucestershire (GB)

(72) Inventors: Steven Streatfield Gill, Bristol (GB); Maxwell Roy Woolley, Bristol (GB); Thomas Gill, Bristol (GB)

(73) Assignee: RENISHAW PLC, Wotton-under-Edge (GB)

( * ) Notice: Subject to any disclaimer, the term of this patent is extended or adjusted under 35 U.S.C. 154(b) by 464 days.

(21) Appl. No.: 14/416,177

(22) PCT Filed: Jul. 24, 2013

(86) PCT No.: PCT/GB2013/051973
§ 371 (c)(1),
(2) Date: Jan. 21, 2015

(87) PCT Pub. No.: WO2014/016591
PCT Pub. Date: Jan. 30, 2014

(65) Prior Publication Data
US 2015/0165166 A1     Jun. 18, 2015

(30) Foreign Application Priority Data

Jul. 24, 2012  (GB) .................................. 1213170.2
Aug. 24, 2012  (GB) .................................. 1215092.6
May 2, 2013   (GB) .................................. 1307921.5

(51) Int. Cl.
*A61M 25/06* (2006.01)
*A61B 17/34* (2006.01)
(Continued)

(52) U.S. Cl.
CPC ..... *A61M 25/0662* (2013.01); *A61B 17/3415* (2013.01); *A61B 17/3421* (2013.01);
(Continued)

(58) Field of Classification Search
CPC ...... A61M 2210/0693; A61M 25/0662; A61M 2025/0681; A61B 2090/103; A61B 90/11
See application file for complete search history.

(56) References Cited

U.S. PATENT DOCUMENTS 4,230,123 A   10/1980  Hawkins, Jr.
4,613,324 A    9/1986  Ghajar
(Continued)

FOREIGN PATENT DOCUMENTS

CN    1672649 A       9/2005
EP    0 266 091 A2    5/1988
(Continued)

OTHER PUBLICATIONS

Raghavan et al., "Convection-enhanced delivery of therapeutics for brain disease, and its optimization", Neurosurgical Focus, Apr. 2006, pp. 1-13, vol. 20, Issue No. 3.
(Continued)

*Primary Examiner* — Emily L Schmidt
(74) *Attorney, Agent, or Firm* — Oliff PLC

(57) ABSTRACT

A neurosurgical kit includes a catheter and a guide tub. The catheter includes a distal section of tubing having a distal end with a port or ports for delivering fluid to a target site within the brain. The distal section of tubing has an outer diameter that is smaller than an internal diameter of the guide tube. The catheter and guide tube are arranged such that, when the catheter is inserted into the guide tube to locate the port or ports at the target site, a recess is provided in a distal end section of the guide tube between the guide tube and the distal section of tubing of the catheter.

16 Claims, 12 Drawing Sheets

(51) Int. Cl.
*A61M 25/00* (2006.01)
*A61B 90/10* (2016.01)
*A61B 90/11* (2016.01)
*A61B 90/00* (2016.01)

(52) U.S. Cl.
CPC ...... *A61B 17/3439* (2013.01); *A61B 17/3494* (2013.01); *A61M 25/0029* (2013.01); *A61B 90/11* (2016.02); *A61B 2017/3407* (2013.01); *A61B 2017/3419* (2013.01); *A61B 2017/3443* (2013.01); *A61B 2090/034* (2016.02); *A61B 2090/103* (2016.02); *A61M 25/0017* (2013.01); *A61M 25/0021* (2013.01); *A61M 2025/0006* (2013.01); *A61M 2025/0008* (2013.01); *A61M 2025/0681* (2013.01); *A61M 2210/0693* (2013.01)

(56) References Cited

U.S. PATENT DOCUMENTS

| | | | |
|---|---|---|---|
| 4,659,329 A | 4/1987 | Annis | |
| 4,850,974 A | 7/1989 | Bickelhaupt et al. | |
| 5,207,648 A | 5/1993 | Gross | |
| 5,312,356 A | 5/1994 | Engelson et al. | |
| 5,380,290 A * | 1/1995 | Makower | A61M 25/06 604/160 |
| 5,409,455 A | 4/1995 | Belden | |
| 5,437,644 A | 8/1995 | Nobles | |
| 5,759,173 A | 6/1998 | Preissman et al. | |
| 5,797,858 A | 8/1998 | Rourke | |
| 5,891,100 A | 4/1999 | Fleckenstein | |
| 6,030,369 A | 2/2000 | Engelson et al. | |
| 6,080,134 A | 6/2000 | Lotti et al. | |
| 6,086,008 A | 7/2000 | Gray et al. | |
| 6,203,526 B1 | 3/2001 | McBeth et al. | |
| 6,203,537 B1 | 3/2001 | Adrian | |
| 6,217,557 B1 | 4/2001 | Håkansson et al. | |
| 6,582,400 B1 | 6/2003 | Hawk et al. | |
| 6,609,020 B2 | 8/2003 | Gill | |
| 6,652,548 B2 | 11/2003 | Evans et al. | |
| 6,926,711 B2 | 8/2005 | Lentz et al. | |
| 2003/0009208 A1 | 1/2003 | Snyder et al. | |
| 2003/0055447 A1 | 3/2003 | Lee et al. | |
| 2003/0093011 A1 | 5/2003 | Jalisi | |
| 2003/0109823 A1 | 6/2003 | Hobot et al. | |
| 2004/0073154 A1 | 4/2004 | Borgesen | |
| 2004/0215162 A1 | 10/2004 | Putz | |
| 2005/0004554 A1 | 1/2005 | Osborne | |
| 2005/0004556 A1 | 1/2005 | Pursley | |
| 2005/0061329 A1 | 3/2005 | Tran et al. | |
| 2005/0154297 A1 | 7/2005 | Gill | |
| 2005/0256508 A1 | 11/2005 | Hall | |
| 2006/0025752 A1 | 2/2006 | Broaddus et al. | |
| 2006/0129126 A1 | 6/2006 | Kaplitt et al. | |
| 2006/0135945 A1 | 6/2006 | Bankiewicz et al. | |
| 2006/0217664 A1 | 9/2006 | Hattler et al. | |
| 2007/0016100 A1 | 1/2007 | Miller | |
| 2007/0276340 A1 | 11/2007 | Poston et al. | |
| 2009/0088695 A1 | 4/2009 | Kapur et al. | |
| 2009/0143764 A1* | 6/2009 | Nelson | A61M 5/14276 604/510 |
| 2009/0198218 A1* | 8/2009 | Gill | A61L 31/028 604/524 |
| 2010/0318061 A1* | 12/2010 | Derrick | A61B 90/11 604/508 |
| 2010/0318064 A1* | 12/2010 | Derrick | A61L 29/16 604/523 |
| 2011/0282319 A1 | 11/2011 | Gill | |
| 2013/0158578 A1 | 6/2013 | Ghodke et al. | |
| 2014/0171760 A1 | 6/2014 | Singh et al. | |
| 2014/0171902 A1 | 6/2014 | Singh et al. | |

FOREIGN PATENT DOCUMENTS

| | | |
|---|---|---|
| EP | 0 643 979 A1 | 3/1995 |
| EP | 0 597 341 B1 | 1/1997 |
| EP | 1155708 A2 | 11/2001 |
| EP | 1155708 A3 | 11/2001 |
| EP | 2258437 A1 | 12/2010 |
| FR | 2 530 958 A1 | 2/1984 |
| GB | 1 530 324 A | 10/1978 |
| GB | 2 008 411 A | 6/1979 |
| GB | 2 132 898 A | 7/1984 |
| GB | 2 330 078 A | 4/1999 |
| GB | 2 355 665 A | 5/2001 |
| JP | 2005-323658 A | 11/2005 |
| JP | 2009-507531 A | 2/2009 |
| JP | 2010-201233 A | 1/2010 |
| WO | 99/34855 A1 | 7/1999 |
| WO | 99/55408 A1 | 11/1999 |
| WO | 03/077764 A1 | 9/2003 |
| WO | 03/077785 A1 | 9/2003 |
| WO | 03077784 A1 | 9/2003 |
| WO | 2005/035043 A2 | 4/2005 |
| WO | 2007/024841 A2 | 3/2007 |
| WO | 2007/024841 A3 | 3/2007 |
| WO | 2007/133776 | 11/2007 |
| WO | 2008/020241 | 2/2008 |
| WO | 2009/101397 | 8/2009 |
| WO | 2012/031275 A2 | 3/2012 |
| WO | 2012/031275 A3 | 3/2012 |

OTHER PUBLICATIONS

Apr. 12, 2013 Search Report issued in European Application No. EP 13 00 1067.
U.S. Appl. No. 12/310,210, filed Feb. 17, 2009 in the name of Gill et al.
Jul. 17, 2014 Office Action issued in U.S. Appl. No. 12/310,210.
Oct. 4, 2012 Office Action issued in U.S. Appl. No. 12/310,210.
Jul. 14, 2009 Office Action issued in U.S. Appl. No. 12/310,210.
Mar. 11, 2015 Office Action issued in U.S. Appl. No. 12/310,210.
Jun. 6, 2013 Office Action issued in U.S. Appl. No. 12/310,210.
Apr. 8, 2010 Office Action issued in U.S. Appl. No. 12/310,210.
Nov. 8, 2016 Office Action issued in European Patent Application No. 13 742 700.1.
Apr. 25, 2017 Office Action issued in Chinese Patent Application No. 201380044196.8.
Jun. 6, 2017 Office Action issued in Indian Patent Application No. 1149/DELNP/2009.
Jul. 26, 2017 Office Action Issued in U.S Appl. No. 15/235,632.
Jun. 27, 2017 Office Action issued in Japanese Patent Application No. 2015-523612.
Bankiewicz KS, Eberling JL, Kohutnicka M, Jagust W, Pivirotto P, Bringas J, Cunningham J, Budinger TF, Harvey-White J. Convection-enhanced delivery of AAV vector in parkinsonian monkeys; in vivo detection of gene expression and restoration of dopaminergic function using pro-drug approach. Experimental neurology, 2000; 164: 2-14.
Barua NU, Bienemann AS, Hesketh S, Wyatt MJ, Castrique E, Love S, Gill SS. Intrastriatal convection-enhanced delivery results in widespread perivascular distribution in a pre-clinical model. Fluids Barriers CNS, 2012; 9: 2.
Bienemann A, White E, Woolley M, Castrique E, Johnson DE, Wyatt M, Murray G, Taylor H, Barua N, Gill SS. The development of an implantable catheter system for chronic or intermittent convection-enhanced delivery. Journal of neuroscience methods, 2012; 203: 284-91.
Bobo RH, Laske DW, Akbasak A, Morrison PF, Dedrick RL, Oldfield EH. Convectionenhanced delivery of macromolecules in the brain. Proceedings of the National Academy of Sciences of the United States of America, 1994; 91: 2076-80.
Chen MY, Lonser RR, Morrison PF, Governale LS, Oldfield EH. Variables affecting convection-enhanced delivery to the striatum: a systematic examination of rate of infusion, cannula size, infusate concentration, and tissue-cannula sealing time. Journal of neurosurgery, 1999; 90: 315-20.

(56) References Cited

OTHER PUBLICATIONS

Degen JW, Walbridge S, Vortmeyer AO, Oldfield EH, Lonser RR. Safety and efficacy of convection-enhanced delivery of gemcitabine or carboplatin in a malignant glioma model in rats. Journal of neurosurgery, 2003; 99: 893-8.

Gill SS, Patel NK, Hotton GR, O'Sullivan K, McCarter R, Bunnage M, Brooks DJ, Svendsen CN, Heywood P. Direct brain infusion of glial cell line-derived neurotrophic factor in Parkinson disease. Nat Med, 2003; 9: 589-95.

Krauze MT, Saito R, Noble C, Bringas J, Forsayeth J, McKnight TR, Park J, Bankiewicz KS. Effects of the perivascular space on convection-enhanced delivery of liposomes in primate putamen. Experimental neurology, 2005a; 196: 104-11.

Krauze MT, Saito R, Noble C, Tamas M, Bringas J, Park JW, Berger MS, Bankiewicz K. Reflux-free cannula for convection-enhanced high-speed delivery of therapeutic agents. Journal of neurosurgery, 2005b; 103: 923-9.

Lang AE, Gill S, Patel NK, Lozano A, Nutt JG, Penn R, Brooks DJ, Hotton G, Moro E, Heywood P, Brodsky MA, Burchiel K, Kelly P, Dalvi A, Scott B, Stacy M, Turner D, Wooten VG, Elias WJ, Laws ER, Dhawan V, Stoessl AJ, Matcham J, Coffey RJ, Traub M. Randomized controlled trial of intraputamental glial cell line-derived neurotrophic factor infusion in Parkinson disease. Annals of neurology, 2006; 59: 459-66.

Lidar Z, Mardor Y, Jonas T, Pfeffer R, Faibel M, Nass D, Hadani M, Ram Z. Convectionenhanced delivery of paclitaxel for the treatment of recurrent malignant glioma: a phase I/II clinical study. Journal of neurosurgery, 2004; 100: 472-9.

Morrison PF, Chen MY Chadwick RS, Lonser RR, Oldfield EH. Focal delivery during direct infusion to brain: role of low rate, catheter diameter, and tissue mechanics. The American journal of physiology, 1999; 277: R1218-29.

Richardson RM, Kells AP, Rosenbluth KH, Salegio EA, Fiandaca MS, Larson PS, Starr PA, Martin AJ, Lonser RR, Federoff HJ, Forsayeth JR, Bankiewicz KS. Interventional MRI-guided Putaminal Delivery of AAV2-GDNF for a Planned Clinical Trial in Parkinson's Disease. Mol Ther, 2011.

San Sebastian W, Richardson RM, Kells AP, Lamarre C, Bringas J, Pivirotto P, Salegio EA, Dearmond SJ, Forsayeth J, Bankiewicz KS. Safety and tolerabillity of magnetic resonance imaging-guided convection-enhanced delivery of AAV2-hAADC with a novel delivery platform in nonhuman primate striatum. Human gene therapy, 2012; 23: 210-7.

Sillay K, Schomberg D, Hinchman A, Kumbier L, Ross C, Kubota K, Brodsky E, Miranpuri G. Benchmarking the ERG valve tip and MRI Interventions Smart Flow neurovatheter convection-enhanced delivery system's performance in a gel model of the brain: employong infusion protocols proposed for gene theraphy for Parkinson's disease. J Neural Eng, 2012; 9: 026009.

Tanner PG, Holtmannspotter M, Tonn JC, Goldbrunner R. Effects of drug efflux on convection-enhanced paclitaxel delivery to malignant gliomas: technical note. Neurosurgery, 2007; 61: E880-2.

White E, Bienemann A, Malone J, Megraw L, Bunnun C, Wyatt M, Gill S. An evaluation of the relationships between catheter design and tissue mechanics in achieving highflow convection-enhanced delivery. Journal of neuroscience methods, 2011; 199: 87-97.

White E, Woolley M, Bienemann A, Johnson DE, Wyatt M, Murray G, Taylor H, Gill SS. A robust MRI-compatible system to facilitate hgihly accurate sterotactic administration of therapeutic agents to targets within the brain of a large animal model. Journal of neuroscience methods, 2010.

Yin D, Forsayeth J, Bankiewicz KS. Optimized cannula design and placement for convection-enhanced delivery in rat striatum. Journal of neuroscience methods, 2010a; 187: 46-51.

Yin D, Richardson RM, Fiandaca MS, Bringas J, Forsayeth J, Berger MS, Bankiewicz KS. Cannula placement for effective convection-enhanced delivery in the nonhuman primate thalamus and brainstem: implications for clinical delivery of therapeutics. Journal of neurosurgery, 2010b; 113: 240-8.

Dec. 21, 2012 Search Report issued in British Application No. 1215092.6.

Oct. 3, 2013 International Search Report issued in International Application No. PCT/GB2013/051973.

Jun. 3, 2016 Office Action issued in Chinese Patent Application No. 201380044196.8.

Aug. 30, 2018 Office Action issued in U.S. Appl. No. 15/235,632.
May 29, 2019 Office Action issued in U.S. Appl. No. 15/235,632.
Feb. 5, 2020 Office Action issued in U.S. Appl. No. 15/235,632.

* cited by examiner

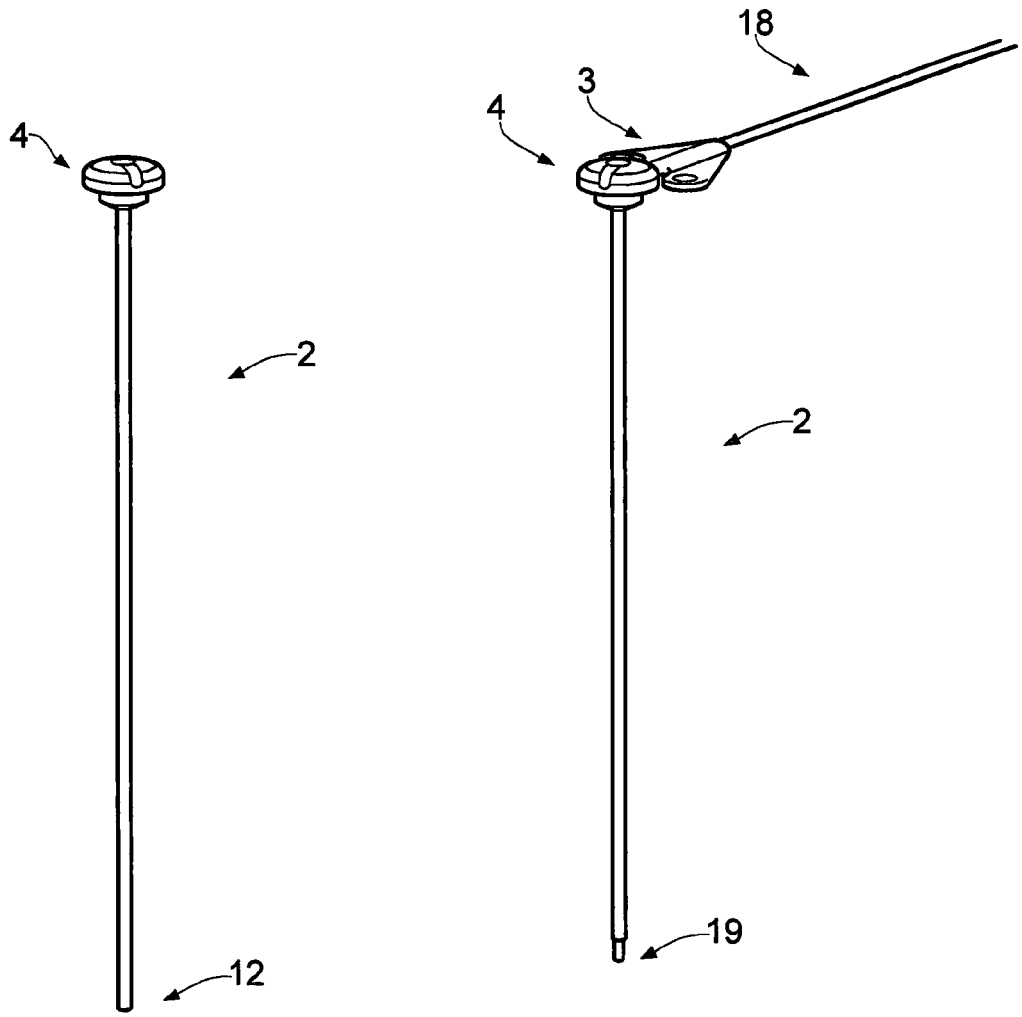

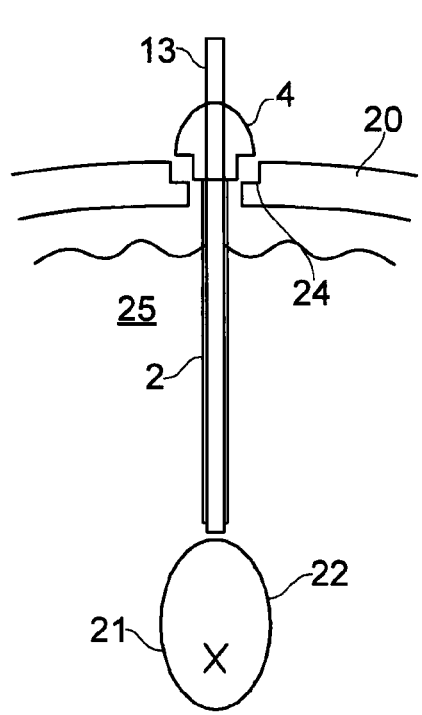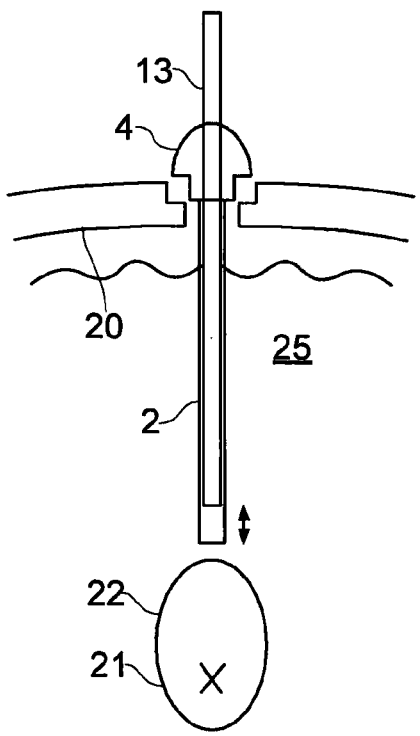
FIG. 5a    FIG. 5b
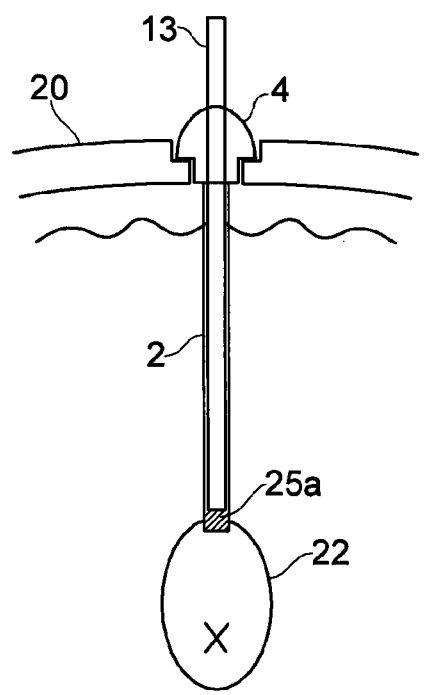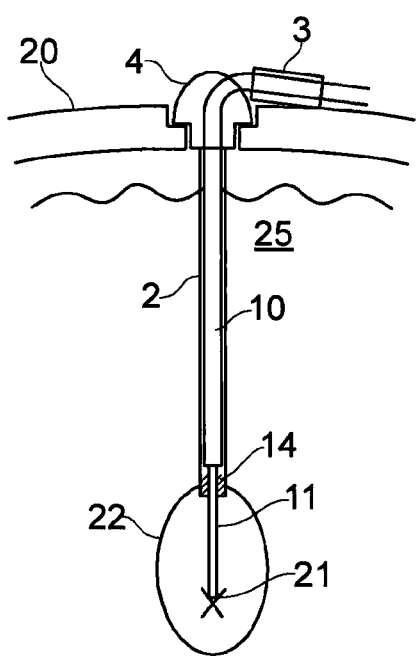
FIG. 5c    FIG. 5d (a)          (b)

NEUROSURGICAL APPARATUS AND METHODS

The present invention relates to neurosurgical apparatus for delivering fluid to the brain, and in particular to improved neurosurgical apparatus that reduces reflux effects. An associated surgical implantation method is also described.

BACKGROUND

Convection enhanced delivery (CED) is a method of delivering drugs to the brain parenchyma using micro-catheters and controlled infusion rates to distribute drugs homogenously through the extracellular space, carried by bulk flow. This method may be used to deliver a wide range of therapeutics for neurological disease that can be targeted to specific brain areas, bypassing the blood brain barrier, and limiting side effects.

Drug distribution by CED is achieved by establishing a pressure gradient at the tip of the catheter that is sufficient to drive infusate through the extracellular space, in preference to it refluxing back along the catheter-tissue interface. To distribute therapeutic agents homogenously through large and clinically relevant volumes, the flow rate needs to be close to the maximum flow rate that the brain can safely tolerate. This is because the pressure gradient drops exponentially from the catheter tip and so to achieve bulk flow one has to establish a sufficient pressure gradient up to the boundary of the desired brain volume whilst competing against dynamic extracellular fluid clearance, particularly through the perivascular spaces, which act as peristaltic pumps. Excessive flow rates at the catheter tip will however result in tissue fracturing, and once this has occurred, the fracture will tend to be propagated in preference to distribution through the extracellular space. In addition, high flow rates are associated with increased reflux along the catheter-tissue interface, and the magnitude of this appears to be related to the extent of tissue trauma produced by catheter insertion and to the catheter's external diameter.

Significant adverse effects have been reported from clinical trials which are directly attributable to reflux of infusate into the subarachnoid space, including chemical meningitis, wound dehiscence and spinal root irritation. Therefore, it is desirable to reduce reflux of the infusate.

Reflux can be reduced when infusing into grey matter at flow rates of up to 5 µl/min, by using catheters that have an outside diameter of approximately 0.4 mm or less. When catheters of larger diameter are employed, they cause greater tissue trauma upon insertion in the annular space around them and through this low resistance pathway the infusate will reflux. However it has also been shown that if a catheter of larger diameter (0.6 mm) is left in situ for sufficient time to allow the tissue to heal, then it's tendency to reflux is substantially reduced.

It is also known that the tendency for a catheter to reflux can be reduced by a gradual ramp up of infusion rate, from a baseline infusion, for example 0.5 µl/min, stepwise over 20 minutes, up to 5 µl/min. It is thought that this gradual expansion of the interstitial spaces, under the influence of positive pressure and fluid content, increases the tissues fluid conductivity, whilst at the same time, the increased tissue pressure may act to improve the tissue seal along the tissue/catheter interface. It is of note that higher flow rates of infusion without reflux can be achieved in white matter than in grey matter (up to 10 µl/min) due to white matter's greater poroelasticity.

Minimising reflux may also be achieved by employing a cannula with a stepped outer diameter with the diameter of the step or steps decreasing from the proximal to the distal end (hereinafter referred to as a "stepped catheter"). The step may prevent or limit reflux along the catheter/tissue interface by focally compressing the tissue to create a seal. For the step to be efficient, the tissue sealing pressure achieved by tissue compression needs to exceed the hydraulic pressure from the refluxing fluid. The longer the length from the distal end of the catheter to the step, the greater will be the reduction in hydraulic pressure at the step. The tissue sealing pressure in the region of the step is likely to be proportional to the diameter change that creates the step. But this needs to be balanced against the tissue trauma that occurs in the region of the step when the cannula is inserted; because disruption of the cyto-architecture provides a low resistance pathway and greater fluid conductivity. An example of such a system is disclosed in WO2007/024841.

SUMMARY OF THE INVENTION

The present invention relates to improved neurological apparatus having one or more of the features described in more detail below.

According to a first aspect of the invention there is provided a neurosurgical kit comprising a catheter and a guide tube. The catheter may comprise a distal section of tubing having a distal end with a port or ports for delivering fluid to a target site within the brain. The distal section of tubing may have an outer diameter that is smaller than an internal diameter of the guide tube and the catheter and guide tube may be arranged such that, when the catheter is inserted into the guide tube to locate the port or ports at the target site, a recess for retaining brain tissue is provided in a distal end section of the guide tube between the guide tube and the distal section of tubing of the catheter.

In use, such a neurological kit may reduce reflux of fluid, such as infusate, along the catheter and guide tube. In particular, the guide tube and catheter may be inserted such that the recess in the guide tube retains brain tissue that acts as a seal against reflux of fluid along the guide tube and catheter. It has been found that providing a seal in this manner may provide improved distribution of fluid delivered using the catheter over a stepped catheter, as described above. Accordingly, the recess may be dimensioned to retain a volume of brain tissue sufficient to act as a seal against reflux along the guide tube of fluid delivered using the catheter. For example, the recess may extend at least 0.5 mm and preferably, about 3 mm into the guide tube. The annulus defined by the guide tube and the distal section of the catheter may have a width (distance between inner and outer walls that form the recess) of at least 0.1 mm and preferably, between 0.1 and 0.5 mm.

The neurological catheter may comprise an indication indicating an extent of the catheter that should be inserted into the guide tube to locate, in use, the port or ports at the target site in the brain, the catheter and guide tube arranged such that, when the catheter is inserted into the guide tube to the extent indicated by the indication, the recess is provided in the distal end section of the guide tube between the guide tube and the distal section of tubing of the catheter. The indication may comprise a stop located on the catheter, the stop engaging a formation on the guide tube to define an extent the catheter can be inserted into the guide tube. The indication may be an indicium on the catheter, which, when aligned at a specified location during insertion of the catheter into the guide tube identifies a position of the catheter in which the port or ports are located at the target site. The provision of an indication may aid in ensuring that the recess is provided, in use.

The neurological kit may comprise a length of tubing having an outer diameter greater than the outer diameter of the distal section of the catheter that defines the recess and an internal diameter less than the internal diameter of the guide tube that defines the recess, the length of tubing located or locatable in the guide tube with a distal end of the length of tubing spaced from a distal end of the guide tube. The length of tubing may close the recess to form a pocket for receiving brain tissue.

The length of tubing may be an intermediate section of the catheter, the catheter comprising an outer diameter that increases from the distal section to an intermediate section of the catheter. The increase in internal diameter may comprise a step between the intermediate section and the distal section of the catheter. Alternatively, the increase in diameter is a gradual increase from the distal section to the intermediate section of the catheter. In this way, the length of tubing is integral with the catheter reducing the number of tubes that have to be inserted into the brain compared to providing the length of tubing as an item separate from the catheter and the guide tube.

The length of tubing may be an intermediate section of the guide tube, an internal diameter of the guide tube decreasing between the distal end section and the intermediate section. The decrease in internal diameter may be a step between the intermediate section and the distal end section of the guide tube. Alternatively, the decrease in diameter may be a gradual decrease from a distal end section to the intermediate section of the guide tube. In this way, the further length of tubing is integral with the guide tubing reducing the number of tubes that have to be inserted into the brain compared to providing the length of tubing as an item separate from the catheter and the guide tube.

The length of tubing may be further tubing separate from the guide tube and catheter, the further tubing arranged, in use, to receive the catheter with the catheter extending through the entire length of the further tubing and to be received in the guide tube such that a distal end of the further length of tubing is spaced from and contained within the guide tube. Providing a further length of tubing may allow the length of the recess to be adjusted by altering the position of the further length of tubing in the guide tube.

An internal diameter of an intermediate section of the guide tube and an outer diameter of an intermediate section of the catheter may be such that the intermediate section of the catheter is a snug fit in the intermediate section of the guide tube.

The distal section of the catheter may comprise a stiff, non-porous tip. The catheter may comprise a flexible tube leading to the stiff, non-porous tip, the flexible tube having a diameter greater than a diameter of the stiff, non-porous tip.

At least one seal may be provided for sealing a gap between separate tubes of the system. For example, a seal may be provided between the catheter and the guide tube, catheter and intermediate tube and/or intermediate tube and guide tube. The seal may be formed integrally with one of the tubes and or a stop connectable to one of the tubes, such as a tapering section arranged to that engage an element connected to another of the tubes of the system, for example, a hub connected to the guide tube. Alternatively, the seal may be a separate sealing element, such as an o-ring. The separate sealing element may be a push fit in a hub of the catheter system.

The neurological kit may comprise a set of catheters, each catheter of the set having a different length stiff, non-porous tip. In this way, the surgeon can select from the set of catheters the catheter having the appropriate length tip for the planned surgery. In particular, the catheter chosen by the surgeon should have a tip that can extend from a distal end the guide tube to the target site, with a small exposed section of the tip extending into the guide tube to form the recess with the guide tube. The set may comprise catheters whose tip lengths differ in intervals that are approximately the same, for example each interval in tip length may be between 0.5 to 4 mm. The differences in length may be based upon acceptable variations in the length of the recess. For example, for a recess that can have a length of between 1 to 3 mm, the interval between tip lengths of catheters of the set may by 2 mm. In this way, a continuum of distances between the distal end of the guide tube and the target site can be accommodated for between the minimum and maximum tip lengths of catheters of the set.

The intermediate section of the catheter may be positioned such that, when the catheter is inserted into the guide tube to the extent indicated by the indication, the distal end of the guide tube is located at least 0.5 mm from an interface at which the catheter first engages the guide tube.

According to a second aspect of the invention there is provided a neurological device comprising a catheter comprising a distal section of tubing having a distal end with a port or ports for delivering fluid to a target site within a brain, the catheter received in a guide tube such that the port or ports are located at the target site in the brain. The distal section of tubing may have an outer diameter that is smaller than an internal diameter of the guide tube, the distal end section located to provide a recess in a distal end portion of the guide tube between the guide tube and the distal section of tubing of the catheter.

The recess may contain compressed brain tissue. The brain tissue may be isolated from a host animal, for example if the brain has been removed from the host animal, or may be brain tissue of a dead animal.

According to a third aspect of the invention there is provided a neurological kit comprising a guide tube that can be cut to the required length, a catheter comprising a distal section of tubing having a distal end with a port or ports for delivering fluid to a target site within the brain, the distal section of tubing having an outer diameter that is smaller than an internal diameter of the guide tube, and an indication for indicating an extent of the catheter that should be inserted into the guide tube, in use, to locate the port or ports at the target site in the brain and to provide a recess in a distal end section of the guide tube between the guide tube and the distal section of tubing of the catheter, the indication adjustable along a length of the catheter.

According to a fourth aspect of the invention there is provided a method of neurological surgery comprising delivering a tube into a brain such that the tube cores a section of brain tissue and positioning a catheter in the brain such that port or ports at a distal end of a catheter are located at a target site in the brain, the catheter passing through brain tissue cored using the tube.

In this way, the brain tissue forms a seal with the catheter and the guide tube that may prevent reflux along the catheter and guide tube of fluid delivered to the brain using the catheter.

A method may comprise passing a section of the catheter through brain tissue cored using the tube, wherein the section has an outer diameter smaller than an internal diameter of the tube such that a proportion of the brain tissue remains in the tube when the port or ports have been located at the target site. Passing the catheter through tissue that has already been cored using the tube may compress cored brain tissue against the sides of the tube and brain tissue below the tube to enhance the sealing effect.

The tube may be a guide tube used to guide positioning of the catheter in the brain.

Locating the guide tube may comprise delivering the guide tube into the brain in conjunction with a stiffer guide rod or wire, wherein towards the end of delivery, the guide tube is delivered with a distal end of the rod or wire located within and spaced from a distal end of the guide tube such that the guide tube cores a section of the brain as it is delivered. Towards the end of delivery, the guide rod or wire may be moved from a position in which the distal end of the guide rod or wire is aligned with or projecting from a distal end of the guide tube to a position in which the distal end of the guide rod or wire is located within and spaced from a distal end of the guide tube.

According to a fifth aspect of the invention there is provided a method comprising obtaining an image of a patient's brain into which at least one guide tube has been inserted, determining a position of the at least one guide tube from the image and, if there is a significant difference between the position of the guide tube and a pre-planned position, modifying a surgical plan.

Modifying the surgical plan may comprise altering the planned insertion length of the catheter. For example, if the catheter is a catheter comprising an adjustable indication that identifies an extent of the catheter to be inserted, the modification may comprise adjusting the position of the indication. Alternatively, the modification may comprise selecting a different catheter to be inserted into the brain using the at least one guide tube, such as a catheter having a different overall length or a different length stiff tip. Modifying the surgical plan may comprise planning to insert into the patient's brain a replacement guide tube.

The guide tube may comprise material that is visible under an MM and/or CT scan.

According to a sixth aspect of the invention there is provided a method of manufacturing a catheter comprising obtaining an image of a patient's brain, determining a target site and target volume in the patient's brain, determining a trajectory through the patient's brain for insertion of a catheter such that a delivery port of the catheter is located at the target site, determining a length of a guide tube required to deliver the catheter such that a distal end of the guide tube is positioned approximately at or just within a boundary of the target volume and manufacturing a catheter having a stiff non-porous tip, a length of the stiff non-porous tip based upon a length from the distal end of the guide tube to the target site.

The method may comprise fixing in place on the catheter an indication for indicating an extent of the catheter that should be inserted into the guide tube, in use, to locate the port or ports at the target site based upon the length of the guide tube. The tip may have an outer diameter smaller than the inner diameter of the guide tube and the stop may be fixed to a location on the catheter such that, when the catheter is inserted into the guide tube to locate the port or ports at the target site, an exposed proximal section of the tip is located in the guide tube to provide a recess in a distal end section of the guide tube between the guide tube and the proximal section of the tip.

According to a seventh aspect of the invention there is provided a method of manufacturing a catheter system comprising receiving patient data, determining from the patient data a required length for each of a catheter and a guide tube such that, when the catheter is inserted into the guide tube, a port at a distal end of the catheter is located at a target site in the brain and a recess for retaining brain tissue is formed in a distal end section of the guide tube between the guide tube and a distal end section of the catheter and adjusting the catheter and/or guide tube for the respective required lengths.

Adjusting the guide tube and/or catheter may comprise cutting the guide tube and/or catheter to the required lengths and/or adjusting the location of an abutment, such as a stop, on the guide tube and/or catheter that define a length of the guide tube and/or catheter that can be inserted into the brain.

The patient data may comprise an image of the patient's brain. The patient data may comprise a distance of a surface of the patient's skull from a reference point, such as a location on a stereotactic frame and/or a position of a robot. Determining the required length may comprise determining a distance from a reference point to the surface of the patient's skull and cutting the guide tube and catheter based upon the measured distance. A required length for the guide tube and catheter may be initially determined from images of the patient's brain. Images (such as Mill and CT scans) of the patient's brain may provide sufficient accuracy for measuring the location of a target site relative to a reference artefact connected to the patient's skull, such as a stereotactic frame, but may not provide clear images of the patient's skull. Accordingly, for a catheter system that uses the skull as a datum for locating the guide tube and catheter in the brain, it is desirable to identify an accurate location of a surface of the skull. This may be achieved by using a pointing device to identify a location of a surface of the skull relative to the reference artefact via which the relative positions of the target site and surface of the skull can be determined. For example, a robot, which has a known location relative to the stereotactic frame, may control a pointing device of known length to contact the surface of the skull to determine the location of the surface of the skull relative to the robot and therefore, relative to the stereotactic frame. On determination of a relative location of the surface of the skull relative to the target site, the lengths of the guide tube and catheter can be adjusted, for example by cutting, based on the measured length.

According to an eighth aspect of the invention there is provided a method of manufacturing a catheter system comprising determining a location of a target site in the brain relative to a reference artefact attached to the patient's skull from images of the patient, determining a location of the surface of the patient's skull relative to the reference artefact using a pointing device for contacting the surface, determining a measured distance from the surface of the patient's skull to the target site from the location of the target site relative to the reference artefact and the location of the surface of the patient's skull relative to the reference artefact and providing a catheter having a length based upon the measured distance.

The length may be a length of the catheter to be inserted into the brain.

According to a ninth aspect of the invention there is provided a data carrier having thereon instructions, which, when executed by a processor, cause the processor to analyse an image of a guide tube inserted into a brain to determine a trajectory of a catheter to be inserted into the guide tube.

The instructions, when executed by the processor, may cause the processor to determine a required tip length of a catheter for a specified target site in the brain based on a position of the guide tube and trajectory of the catheter as determined from the image.

According to a tenth aspect of the invention there is provided a catheter apparatus comprising a first section of tubing having a distal end. In use, the distal end of the first section of tubing is preferably implanted within the brain. The first section of tubing of the catheter apparatus may be provided by a guide tube device as described in U.S. Pat. No. 6,609,020, the contents of which are hereby incorporated by reference. The guide tube device may thus provide the first section of tubing and may also include a head that is attached to the proximal end of the first section of tubing. The head may include one or more features for attaching the guide tube to the skull. For example, the head may include features that allow it to be retained in a burr hole formed in the skull.

Preferably, the catheter apparatus also comprises a second section of tubing that has a distal end comprising a port or ports for delivering fluid to a target site within the brain. The first and second sections of tubing may be formed as a single, unitary, piece or may be assembled by a surgeon before or during the implantation procedure. The second section of tubing preferably has an outer diameter (OD) less than the outer diameter of the first section of tubing. The second section of tubing preferably has an outer diameter that is smaller than the internal diameter of the first section of tubing. In use, the second section of tubing is preferably at least partially located with the lumen of the first section of tubing and preferably protrudes from the distal end of the first section of tubing. A step in external diameter is thus provided between the first and second sections of tubing. The first and second sections of tubing may be substantially co-axial.

A recess or internal pocket is preferably provided at the distal end of the first section of tubing. This recess preferably surrounds the second section of tubing. The recess may be defined, at least in part, by the internal walls of the first section of tubing. The recess may extend a short distance (e.g. no more than 5 cm, more preferably no more than 3 cm, more preferably no more than 1 cm, more preferably no more than 0.5 mm) into the lumen of the first section of tubing. The aperture at the distal end of the first section of tubing may define an opening of the recess.

In use, brain tissue is preferably located in the recess or pocket. This may be achieved using a coring effect during insertion of the first section of tubing into the brain. The second section of tubing may then be passed through a retained core of brain tissue during the insertion procedure. For example, the second section of tubing may be inserted into the proximal end of the first section of tubing and passed through the first section of tubing until it exits the distal end thereof, thereby piercing the core of brain tissue that is retained in the recess. This arrangement has been found to provide a fluid seal that reduces reflux along the interface between the first section of tubing and the brain tissue in which it is implanted. As explained below, such reflux reduction improves the drug delivery performance of the device.

In a preferred embodiment, the second section of tubing is provided as the distal end of a catheter device. In particular, the catheter device may be a stiff tipped catheter device of the type described in WO2009/101397, the contents of which are hereby incorporated herein by reference. In particular, a catheter device may be provided with a form similar to that shown in FIG. 2 of WO2009/101397 where a stiff silica tube 34 (which provides the second section of tubing) is partially inserted into the end of flexible plastic tube 32. In such an arrangement, the flexible plastic tube 32 may fit snugly within the first section of tubing (e.g. the OD of the flexible plastic tube 32 may be matched to the ID of the guide tube device into which it is inserted to provide a snug fit). In such an example, the distal end of the flexible plastic tube 32 forms an end to the recess defined by the first section of tubing. The distal end of the stiff silica tube 34 can then be arranged to pierce the core of tissue that is held within the recess during insertion through the guide tube device to the target site.

Preferred embodiments of the invention are outlined in the attached drawings. These are provided by way of example only.

BRIEF DESCRIPTION OF THE DRAWINGS

FIG. 1a is a perspective view of a guide tube of neurological apparatus according to one embodiment of the invention;

FIG. 2 shows the neurological apparatus of FIGS. 1a and 1b in an assembled condition;

FIGS. 5a to 5d show schematically a method of inserting the neurological apparatus shown in FIG. 1 into the brain;

DESCRIPTION OF EMBODIMENTS

Figure 1B:
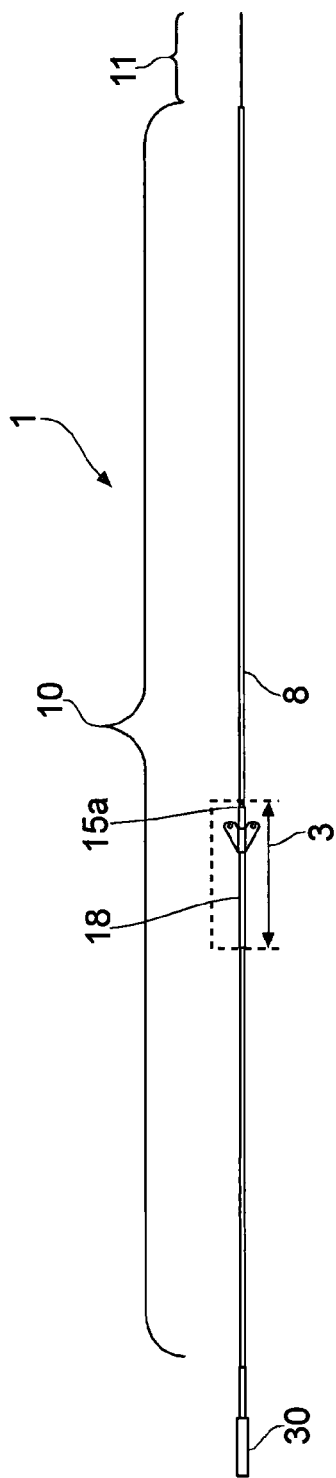
FIG. 1b is a perspective view of a catheter of neurological apparatus according to one embodiment of the invention.
Figure 3A:
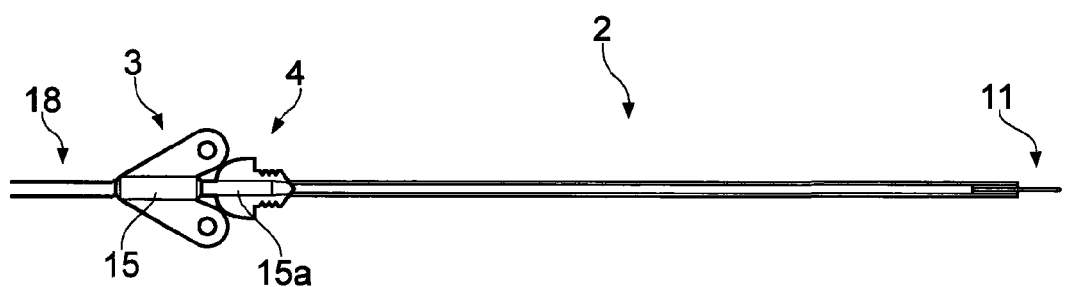
FIG. 3a is a cross-sectional view of the neurological apparatus shown in FIG. 1, when assembled.
Figure 3B:
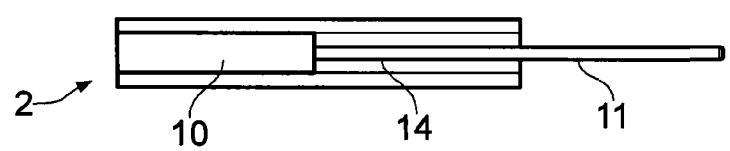
FIG. 3b is a cross-sectional view of a distal end of the neurological apparatus shown in FIG. 1, when assembled.
Figure 3C:
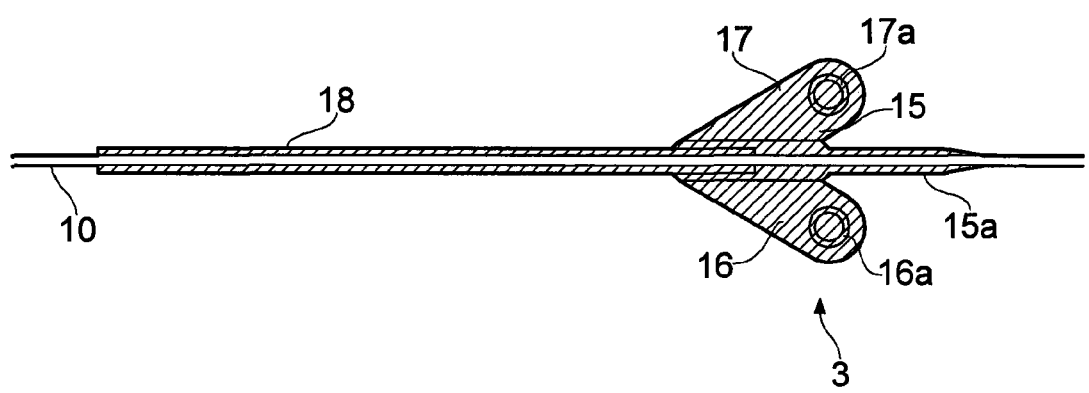
FIG. 3c is a cross-sectional view of a stop section of the neurological apparatus shown in FIG. 1.
Figure 4:
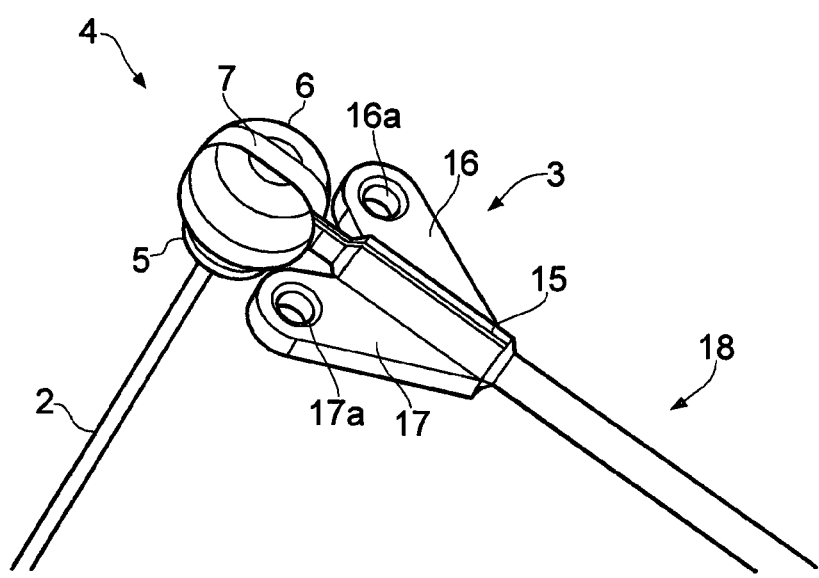
FIG. 4 shows a hub and stop of the neurological apparatus shown in FIG. 1.

Referring to FIGS. 1 to 4, the neurosurgical apparatus comprises an indwelling catheter 1, a guide tube 2 and a winged stop 3.

The guide tube 2 is made of carbothane and, in this embodiment, has a 1 mm outside diameter and a constant 0.6 mm internal diameter. At its proximal end there is a hub 4 with a smaller diameter distal section 5, which in this embodiment is threaded, and a larger diameter proximal section 6 in the form of a dome having a slot 7 running diametrically across the dome. This is most clearly illustrated in FIGS. 3 and 4. The floor (not shown) of the slot 7 has a curvature either side of the bore of the tube 2 that provides continuation of the surface of the bore.

The catheter 1 comprises a fixed length of tubing 8 and, at a proximal end, a boot 30 for attaching the tubing 8 to an infusion tube (not shown) for infusing infusate into the catheter 1. The tubing 8 comprises for the majority of its length a flexible length of tubing 10, in this embodiment made of fluorinated ethylene propylene (FEP) or polyether ether ketone (PEEK) or carbothane, and a stiff, non-porous tip 11, in this embodiment made of fused silica tube with a polyimide coating. The flexible tube 10 is heat-shrunk or bonded onto the tip 11 with the tip 11 extending a fixed length from the flexible tube 10 of between 6 to 60 mm. The tip 11 comprises a port at its distal end for delivering fluid to a target site within the brain. The distal end 19 of the tip 11 may have been laser cut to provide an internal diameter that increases from proximal to distal at the tip 11. The increase in internal diameter may produce a fall-off of pressure and a reduction in the velocity of the fluid as it leaves the catheter 1. The laser cutting of the distal end 19 may also provide a rounded distal end 19, which may cause less tissue trauma on insertion into the brain.

The length of tubing 10 has an outer diameter greater than the outer diameter of the tip 11, which, as described below, defines a recess 14 in the guide tube 2 in use. In this embodiment, the flexible tube 10 has an outside diameter of 0.6 mm and an internal diameter of 0.25 mm and the tip 11 has an outside diameter of 0.235 mm and an internal diameter of 0.15 mm. Accordingly, the tip 11 provides a distal section of tubing of the catheter 1 having an outer diameter that is smaller than an internal diameter of the guide tube 2 and tubing 10 of the catheter is a snug fit in the guide tube 2.

The winged stop 3 is arranged to be adjustable along tubing 10 of the catheter 1. The winged stop 3 comprises a central tubular section 15 for receiving tubing 10 such that the stop 3 can be slid along the tubing 10 and two wings 16, 17 either side the central tubular section 15. The external diameter of the central tubular section 15 tapers towards a distal end 15a. This tapered distal end 15a can form a seal within the hub 4, as described in more detail below. Each wing 16, 17 has a hole 16a, 17a therethrough for receiving screws for fixing the stop 3 to the skull. The proximal end of the stop 3 comprises a length of flexible tubing 18 that is fixed to the central section 15 such that the tubing 18 can slide with the central section 15. The stop 3 can be fixed in place on the tubing 10 by applying an appropriate adhesive, such as a dental acrylic cement, to fix tubing 18 to tubing 10. However, in another embodiment, a clamping mechanism or tie may be provided.

The boot 30 comprises a sleeve of larger diameter than tubing 10 that can be push fitted onto various devices, such as a bayonet connector or a Luer connector.

In use, images, such as Mill and CT images, are taken of the patient's brain and a target site 21 and target volume 22 in the brain are identified. Typically, the target site 21 is between the middle and the bottom ⅔ of the target volume 22. The stereotactic coordinates and trajectory of the catheter 1 are determined based upon the target site 21 and target volume 22 and a coordinate position along the trajectory is determined for the distal end 12 of the guide tube 2. Preferably, the coordinate position for the distal end 12 is just within, such as 2 to 3 mm within, the target volume 22. The required length of the guide tube 2 can be determined from the intended coordinate position of the distal end 12 and the guide tube 2 is cut to this required length.

It may not be possible to determine with sufficient accuracy a location of the surface of the skull relative to the target site from the Mill and CT images of the patient. In particular, the boundary of the skull tends to be unclear in the images. Accordingly, an expected length for the catheter 1 and guide tube 2 may be determined from the images, but this may then be confirmed in theatre before the guide tube 2 is cut to the required length and the stop 3 fixed at the required position on the catheter 1.

In theatre, the relative location of the surface of the skull to the stereotactic frame may be measured by moving a pointing device, for example using a robot, whose location is known relative to the stereotactic frame, to touch the skull. A location of the surface of the skull relative to the stereotactic frame can be determined from the location of the pointing device when contacting the skull. A location of the target site relative to the stereotactic frame can be determined with sufficient accuracy from the images. Accordingly, a distance from the skull to the target site can be confirmed from their known locations relative to the stereotactic frame as determined from the images and using the pointing device.

Once the lengths of the guide tube 2 and catheter 1 have been adjusted, the guide tube 2 is inserted over a guide rod 13, whose length is adjusted by a locking collet (not shown) attached to a distal end of a delivery tool such that a tip of the guide rod projects a short distance, such as 1 mm ahead of the guide tube 2.

The patient's head is fixed within a stereoguide frame and the coordinates and trajectory are set in a stereoguide. Having exposed the skull 20, a hole 24 having a stepped profile is drilled into the skull 20, the profile corresponding to the profile of the hub 4 of the guide tube 2. This stepped profile provides a datum for positioning the guide tube 2 in the brain 25 with the distal end 12 at the required position. The dura and brain cortex are also penetrated to accept the guide rod 13 and guide tube 2.

The guide tube 2 inserted over the guide rod 13 is then inserted into the brain through a hole 24 to a point where the hub 4 first engages the hole 24 formed in the skull 20, as shown in FIG. 5a (the hub 4 being an interference fit in the hole). This point is just short, in this embodiment 2.5 mm short, of full insertion, in which the distal end 12 of the guide tube 2 is located as desired. The guide rod 13 is now withdrawn by 3 mm, shown in FIG. 5b, and the guide tube 2 with the guide rod 13 in this withdrawn position further inserted to the stop position as defined by the engagement of the hub 4 with the profiled hole 24 in the skull 20. In executing this manoeuvre, the distal end 12 of the guide tube 2 cores 1-3 mm of brain tissue. This position is shown in FIG. 5c. The guide rod 13 is then withdrawn leaving the guide tube 2 in position.

With the guide tube 2 in position, an image, such as an MRI image, may be obtained of the patient's brain to check the position of the guide tube 2. If the actual position of the guide tube 2 is dramatically different from the intended position, a new trajectory may have to be planned and a replacement guide tube 2 inserted. If the position of the guide tube 2 is slightly away from the intended position, such as the distal end of the guide tube 2 being slightly deeper or slightly shallower than the intended position, the stop 3 on the catheter 1 can be adjusted to compensate. A trajectory of the catheter 1 may be modelled based on the actual position of the guide tube 2 as determined from the image. This trajectory may be modelled using appropriate modelling software.

The required length of the catheter 1 is known from the planned trajectory and/or image taken of the patient's brain with the guide tube implanted, as is the length of the guide tube 2. A catheter 1 with an appropriate length tip 11 is selected, such as from a set of the catheters with different length tips 11, such that at least 1 mm of the exposed tip 11 (a portion not covered with the flexible tube 10) remains in the guide tube 2 when the catheter 1 is inserted into the guide tube 2 with its distal end located at the target site. The winged stop 3 is glued to the catheter 1 at a position spaced from a distal end of the catheter 1 defined by the distance between the apex of the domed section on hub 4 of the guide tube 2 when fully inserted in the skull and the target site 21.

A trochar (not shown) is tunnelled though the scalp from a site at which the boot 30 of the catheter 1 is to be located to a position adjacent the proximal end the guide tube 2. The proximal end of the catheter 1 is fed into the distal end of the trochar cannula and brought through the scalp with removal of the trochar cannula. The catheter 1 is flushed with infusate after attaching the boot 30 to an infusion line. The catheter 1 is then slowly inserted into the guide tube 2 to the target site whilst at the same time aspirating air that is displaced from the guide tube 2 as the catheter 1 is inserted down the guide tube's bore. The air is aspirated using a surgical sucker, whose tip is applied over one side of the slot 7 of the guide tube's hub 4.

During insertion, tip 11 of the catheter pushes through the brain tissue 25a cored using the guide tube 2 compressing the brain tissue against the guide tube 2 and the brain tissue below. Engagement of the winged stop 3 with the hub 4 of the guide tube 2 indicates that the distal end of the catheter 1 has been inserted to the target site 21. In this position, a recess 14 is provided in a distal end section of the guide tube 2 between the guide tube 2 and tip 11 of the catheter 1. A distal end of tubing 10 is located in the guide tube 2 spaced from the distal end of the guide tube 2. In use, this recess 14 retains brain tissue cored using the guide tube 2.

With the winged stop 3 continuously engaging the hub 4, the catheter 1 is bent through 90° and the winged stop 3 secured to the skull with screws (not shown). The radius of curvature of the dome 6 is the same as the radius of curvature of the slot 7 such that the length of the catheter 1 emerging from the guide tube 2 remains constant during this manoeuvre. This position is shown in FIG. 5d. The scalp wound is now closed and a ramped infusion regime commenced.

Figure 6:
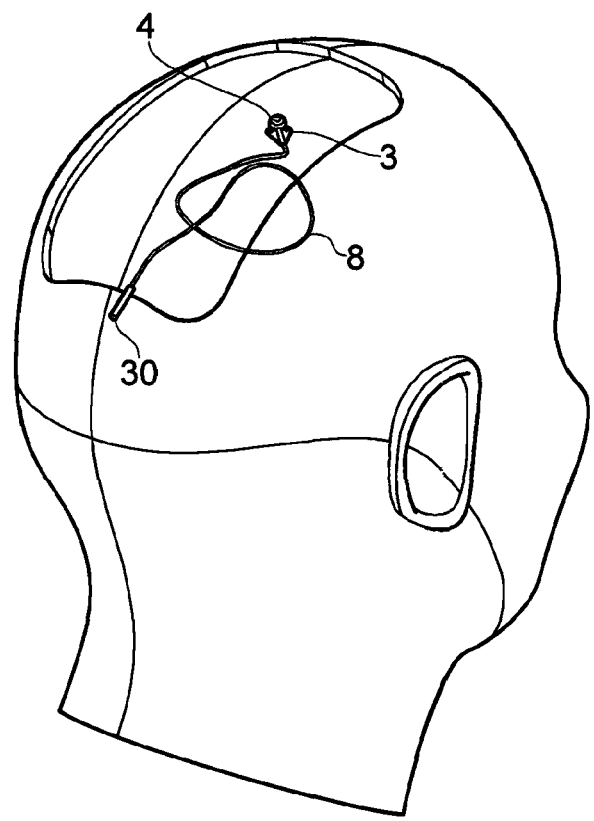
FIG. 6 show neurological apparatus according to the invention in situ.

FIG. 6 illustrates the appearance of the patient after insertion of the apparatus.

EXAMPLE

A neurological apparatus according to the invention (referred to herein as "the recessed catheter") was compared with a 1 mm stepped catheter and a ceramic 0.6 mm stepped catheter. The design of each catheter was similar in that they each had a 3 mm length of fused silica (0.23 mm outside diameter, 0.15 mm inside diameter) extending beyond their distal stepped outer diameter. The 1 mm stepped catheter had the same external profile as the recessed catheter, excluding the recess. The ceramic catheter had a distal step from 0.23 mm to 0.6 mm. The apparatus were evaluated in an agarose gel (0.5%) brain model that has the same pore fraction as brain grey matter. The recessed catheter was subsequently evaluated in a large animal model, a large white landrace pig.

In-Vitro Testing

Materials and Methods

The carbothane guide tube 2 of the recessed catheter was cut to a length of 80 mm, and the indwelling catheter 1 was a PEEK tube (0.6 mm OD/0.25 mm ID) with a fused silica tip 11 (0.23 mm OD/0.15 mm ID) bonded into its distal end, from which it protruded by 6 mm. The stop 7 was applied to the PEEK tube 77 mm from its distal end, so that when it was inserted into the guide tube 2, a 3 mm recess was created, down the central axis of which the fused silica tip 11 traversed, and extended 3 mm beyond the distal end of the guide tube 2.

The 1 mm step catheter was of similar construction to the recessed catheter, with the exception that the length of the PEEK tube distal to the stop was 80 mm, and the length of protruding fused silica was 3 mm. On insertion therefore, the distal end of the guide tube and the PEEK catheter were flush, and together formed a step, from which the fused silica tube extended by 3 mm.

The ceramic 0.6 mm stepped catheter comprised a 77 mm ceramic tube that encased a length of fused silica tube (0.23 mm outside diameter, 1.5 mm inside diameter) except for 3 mm, which protruded from its distal end. The ceramic tube had a stepped outer profile reducing from an outside diameter of 1.3 mm to 0.6 mm at a distance of 10 mm from its distal end. A length of FEP tubing extended from the proximal end of the ceramic catheter for connection to a Hamilton syringe.

Agarose gel 0.5% was made by mixing 4.05 g Molecular Biology grade agarose powder (Severn Biotech), 67.5 ml Trist Borate EDTA Buffer (Severn Biotech) with 607.5 ml of deionised water and poured into a Perspex container and allowed to set. A Perspex lid was secured to the container and the container fixed to a platform within a stereo guide (Cosman Roberts Wells, Radionics Inc.).

A step-profile drill was introduced through the stereo-guide and used to create a hole in the Perspex lid of the agarose container which acted as a guide to deliver the guide tube into the gel and also to form a recess in the lid into which the guide tube's hub was press fitted. Two such holes were made in the 'lid' set several centimetres apart, one for the recessed catheter and the other for the 1 mm step catheter. A 1.35 mm diameter drill hole was made in the Perspex lid through which to introduce the ceramic 0.6 mm stepped catheter.

The guide tubes for both the 1 mm stepped and the recessed catheters were inserted through the pre-made holes in the Perspex lid and into the agarose gel using a delivery tool, that itself was guided by the stereo-guide. The delivery tool comprised a cylindrical body with a co-axial 0.6 mm guide rod that could be adjustably extended beyond its distal end and over which the guide tube was placed during insertion. The distal end of the guide rod was rounded, and extended beyond the distal end of the guide tube by 1 mm. The method of insertion of the guide tube differed depending on whether it was used for the recessed catheter or the 1 mm stepped catheter. When inserting the guide tube for the recessed catheter, insertion along the trajectory was stopped at the point when the guide tube hub first engaged with the recess in the Perspex lid i.e. 2.5 mm short of full insertion. At this point, the 0.6 mm guide rod was withdrawn by 3 mm and re-secured within the cylindrical body of the delivery tool. The guide tube was now advanced to its stop position, and in so doing, it cored a 1.5 mm cylinder of agarose that plugged the distal end of the guide tube. When inserting the guide tube for the 1 mm step catheter, insertion is stopped when the guide tube is 1 mm short of target, at which point the guide rod is withdrawn by 1 mm, and the guide tube is now pushed home. As the guide rod had extended 1 mm in advance of the guide tube, prior to the 1 mm advance, no coring action will occur.

The catheters were connected at their proximal ends to Hamilton syringes, filled with a 0.04% solution of trypan blue. The Hamilton syringes were loaded into twin drive CMA 402 syringe pumps (Harvard Apparatus Company, Solna, Sweden), and the catheters primed. The infusion was commenced at 0.5 µl/min, and each catheter was then slowly inserted. The catheters were infused during their insertion, so as to prevent their distal tips occluding, and once fully inserted, the infusions were stopped. It's of note that whilst the inner catheter elements of the recessed step catheter and the 1 mm step catheter were introduced down their respective guide tubes suction was applied to the slot in the hub, so as to prevent air being driven into the agarose by a piston action on insertion.

A digital camera (Canon SD 100) was positioned and secured at a fixed distance from the agarose filled Perspex box and the infusions commenced simultaneously using a ramp up regime over 25 minutes, up to a maximum flow rate of 5 µl/min, which was maintained until a total volume of 300 µl had been delivered (see Table 1). Images of the infusions were taken at commencement and sequentially after every 25 µl had been infused in each catheter. This experiment was repeated 10 times.

TABLE 1

| Flow Rate µL/Min | Time Increment Min | Total Time Min | Total Volume µL |
|---|---|---|---|
| 0.5 | 10 | 10 | 5 |
| 1.0 | 5 | 15 | 10 |
| 2.0 | 5 | 20 | 20 |
| 3.0 | 5 | 25 | 35 |
| 5.0 | Continue until a total volume of 300 µL is delivered | | |

From magnified digital images an estimate was made of the volume of distribution from each catheter below the first step i.e. 3 mm from the distal tip of the fused silica. The volume of distribution was calculated by measuring the transverse diameter of the infusion cloud at its widest, and its vertical diameter below the step and assuming it to be a spheroid. The equation for the volume calculation is shown below.

$$\text{volume: } \frac{4}{3} \cdot \pi \cdot ab^2,$$

where 'a'=half the measured height of the infusion below the step and b=half the measured diameter of the infusion, assuming that the diameter is constant in the axial plane. The volume of the 3 mm length of fused silica was subtracted from each volume calculation.

An estimate of the volume into which the infusate had refluxed was calculated by measuring the height and mean diameter of contrast above the step to determine a mean cylindrical volume, from which the volume of that length of guide tube was subtracted. The mean diameter of the reflux volume was determined by making measurements at 3 mm intervals along the length of reflux from the distal end of the guide tube.

The data was analysed to determine whether there was significant difference in catheter performance, i.e. reflux resistance and volume of distribution between the recessed step design, the 1 mm step and 0.6 mm step design.

Figure 7:
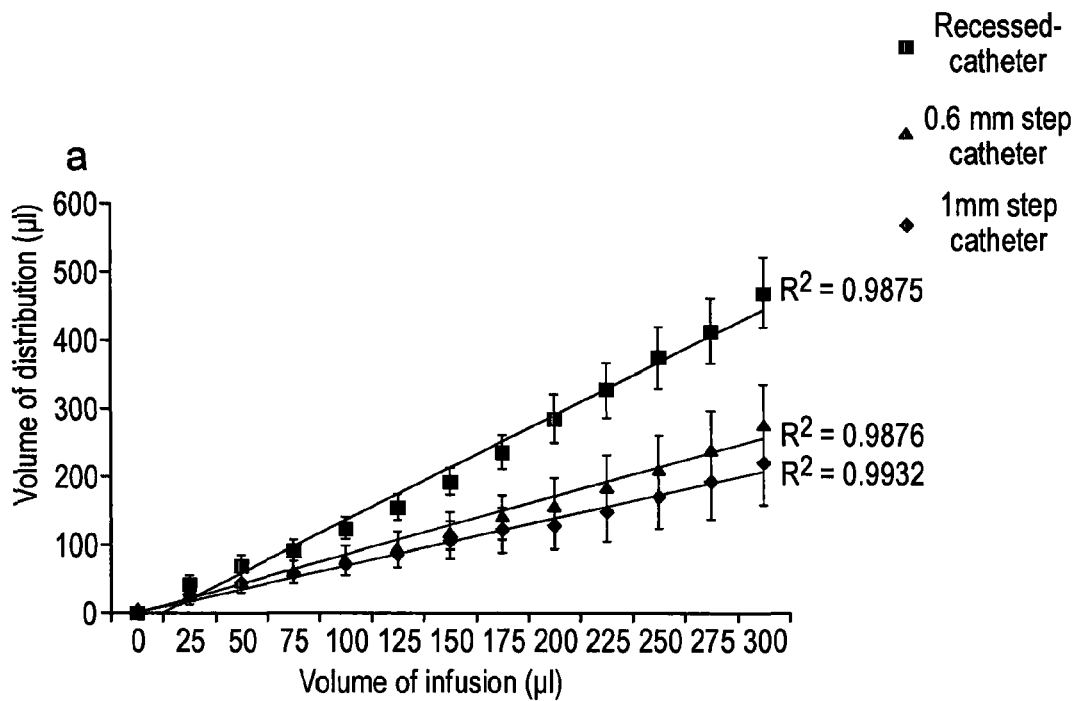
FIG. 7 is a graph showing volume of distribution versus volume of infusion for a recessed catheter, 1 mm stepped catheter and 0.6 mm stepped catheter.
Figure 8:
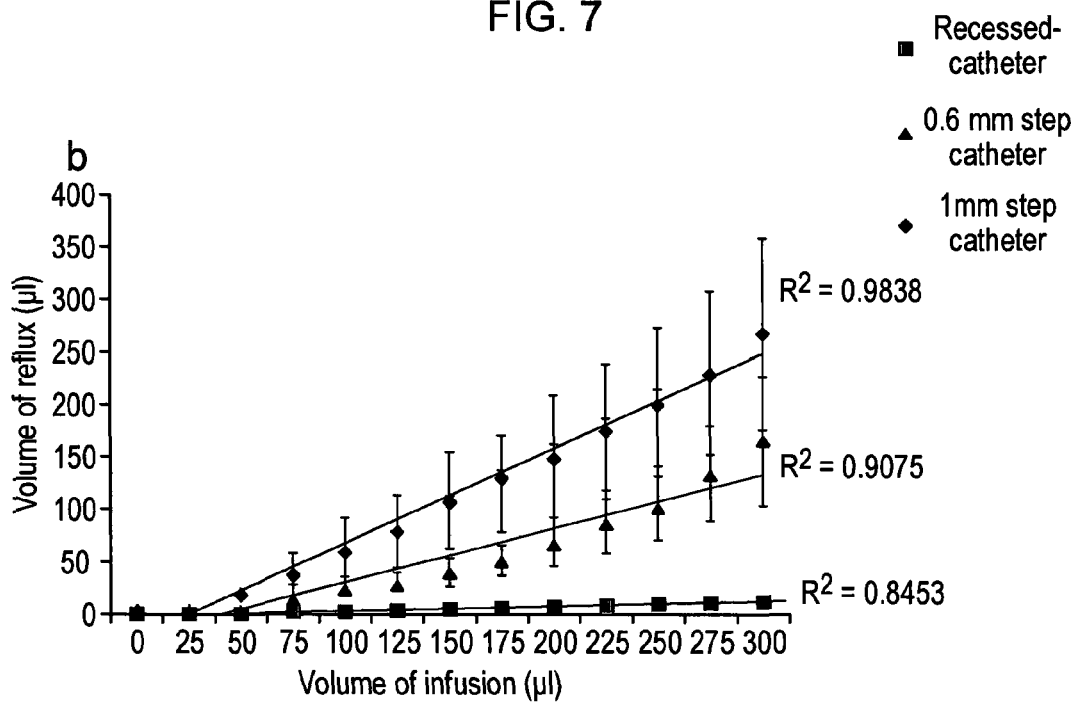
FIG. 8 is a graph showing volume of reflux versus volume of infusion for a recessed catheter, 1 mm stepped catheter and 0.6 mm stepped catheter.

Results:

The results comparing the volume of distribution between the recessed step catheter and the stepped catheter are shown in FIGS. 7 and 8.

The recessed catheter achieved on average a 2.25 fold greater volume of distribution than was achieved with the 1 mm step catheter and a 2 fold greater volume of distribution than the 0.6 mm step catheter after infusing 300 µl. The difference in catheter performance became significant shortly after the ramp up to 5 µl/min when approximately 50 µl had been infused and the non recessed step catheters began to reflux.

By completion of the 300 µl infusions only 2% of the volume of distribution of the recessed catheter was attributed to reflux whereas for the 1 mm stepped it was 54% and for the 0.6 mm step catheter it was 36%. Although there was a significant difference in Vd/Vi below the step between the recessed catheter and the 1 mm and 0.6 mm stepped catheter designs there was no significant difference between the latter 2 stepped catheters. During the infusions however between 100 and 225 µl of infusion the 0.6 mm step catheter showed significantly less reflux than the 1 mm step catheter but this significance was lost as the volume of infusion increased to 300 µl.

Discussion

Typically, for both the recessed and 1 mm step catheters, on commencement of the infusion, a small spherical volume of distribution was seen at the tip of the fused silica. Thereafter, micro-reflux became visible, extending proximally towards the step. The spherical shape then evolved into a teardrop as it expanded. When the apex of the teardrop had extended to the step, which generally occurred at the end of the ramp up phase the performance of each catheter then differed.

In the case of the 1 mm step catheter, infusate began to extend radially along the under surface of the step and then began to reflux back along the outside surface of the guide tube whilst the teardrop shaped infusion volume continued to expand. The teardrop subsequently merged with the reflux to form an ovoid, and increasing cylindrical shape, as the degree of reflux proportionately increased.

Counter intuitively the 0.6 mm step was initially more effective than the 1 mm step in resisting reflux with 3 of the 10 infusions showing little reflux and generating relatively spherical volumes of distribution below the step. When the 0.6 mm step was overwhelmed the second step up to 1.3 mm diameter, which was positioned 10 mm proximally along the shaft, was effective in inhibiting further reflux beyond this point. An explanation for the difference in performance between the 1 mm and the 0.6 mm steps in limiting reflux is that, upon insertion, the larger diameter displaces a greater volume of agarose gel and in doing so it is more likely to disrupt its structure forming low resistance pathways through which the infusate will preferentially flow. So although a step, by focally compressing tissue can improve the seal around a catheter disruption of the tissue by too larger step change, or traumatic catheter insertion may have a converse effect.

Performance of the recessed catheter differed from conventional stepped catheters in that when the apex of the teardrop reached the point at which the fused silica entered the distal end of the guide tube, reflux was inhibited presumably by greater compression of the agarose against the fused silica within the recess. The teardrop shape then became increasingly spherical and continued to expand with very little reflux evident along the outside of the guide tube. If this did occur, micro-reflux was observed in a very narrow annular space around the distal 3 mm of the guide tube and then expanded into a larger annular volume of agarose gel that extended variably along the remainder of the guide tube. The explanation for this is that the distal 3 mm of the guide tube, in coring the agarose gel, had minimally displaced it, and created an effective tissue seal, whereas more proximally, where the guide tube had been inserted with an indwelling guide rod, the combined volume had been displaced radially, which had caused disruption of the agarose gel, and consequently had created a low resistance pathway, along which infusate could reflux.

Figure 9:
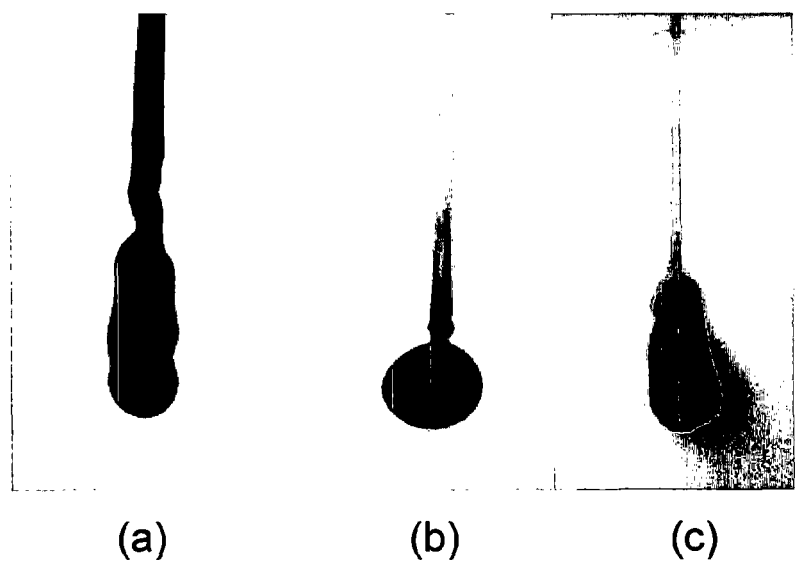
FIG. 9 are images showing typical infusion profiles for (a) a 1 mm stepped catheter, (b) a recessed catheter and (c) a 0.6 mm stepped catheter after 300 μm of trypan blue has been infused in 0.6% agarose gel.
Figure 10:
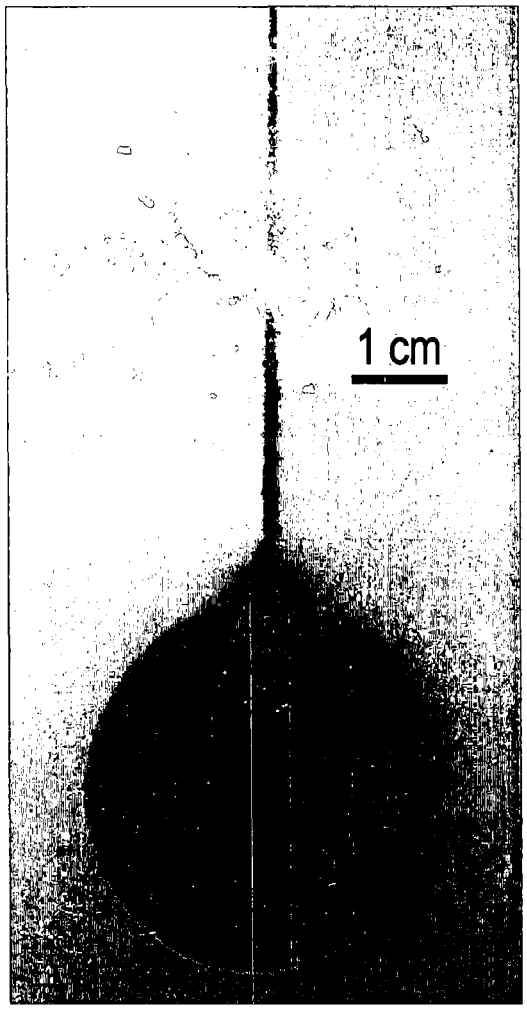
FIG. 10 is an image showing distribution of 15,500 μl of fluid after being infused using a recessed catheter with a 15 mm tip.

The distribution of fluid infused into the agarose gel using the catheters is shown in FIGS. 9 and 10.

In Vivo Testing

The recessed catheter was evaluated by implanting it into the putamen of a pig bilaterally, and its performance compared with a 1 mm stepped catheter, also implanted into the putamen of the pig.

The recessed catheter and delivery tooling was as described above, and had a recess length of 3 mm.

Materials and Methods

Two 45 kg male large white landrace pigs were used in this study. The study was carried out in accordance to the UK scientific procedures act 1986, under appropriate project and personal licences. Animals were sedated with intramuscular ketamine (10 mg/kg) incubated and subsequently anaesthetized with 1.5-5% isoflourane.

A head fixation device was applied to each pig. This employs a dental tray for the upper jaw, with a snout strap, and zygomatic screws to immobilize the head. Each animal was then positioned on an Mill scanner table (Phillips 1.5T), to which the head immobilization device was secured. A fiducial system was the attached to the head frame and Flex-L head coils positioned around the head. A series of contiguous T1-weighted coronal slices (1 mm slice thickness) of the pigs' heads, including fiducials, were acquired from which targets and trajectories were selected for catheter placement, using planning software (Mayfield ACCISS-II UK). Typically the targets were in the ventral third of the mid-portion of the putamen on each side. The animals were then transferred to the operating theatre where the head fixation device was fixed to a datum on a platform, that itself was rigidly fixed to a Pathfinder surgical robot (Prosurgics UK). The animal's scalp was prepared and draped and a U shaped incision was made, to expose the skull surface. The stereotactic co-ordinates and trajectory of the deep putamenal target were transposed to the robotic arm and a stepped drill was inserted down the stereo guide to form a profiled burr hole in the skull. The guide tube and catheter were then delivered to the target as previously described. This was repeated on the contralateral side. Both putamenal catheters were positioned such that the step position, i.e. the distal end of each guide tube, was 2 mm within the dorsal putamen and the fused silica extended beyond the step position by 3 mm. The pig was repositioned on the MM bed and the putamen were bilaterally infused with Gd-DTPA (Magnevist: Bayer Healthcare Germany) in artificial CSF to a concentration of 0.25%, using the ramping regime as illustrated in table 1, and infusions were continued until significant reflux along the catheters were seen. During the infusions, sequential T1 weighted Mill images were acquired and at the end of each acquisition, the total volume infused was recorded.

The volume of distribution/volume of infusion (Vd/Vi) for each catheter was determined from each image acquisition by summating the areas of contrast measured on each slice (1 mm contiguous slices). These calculations were made using in-house software.

Results

The recessed catheters were introduced without complications and image analysis showed a linear increase in volume of distribution with time (with Vd/Vi≈2.75)). No reflux was identified after infusion of 587.5 µl per catheter by which time the volume of distribution from each catheter was around 1500 mm$^3$ and the putamen were full of contrast. The experiment was stopped at this time as no further useful information could be obtained. The catheters were removed, the wound closed and anaesthesia reversed. The pig recovered without any detected neurological deficit. The results are shown graphically in FIG. 11.

Figure 11:
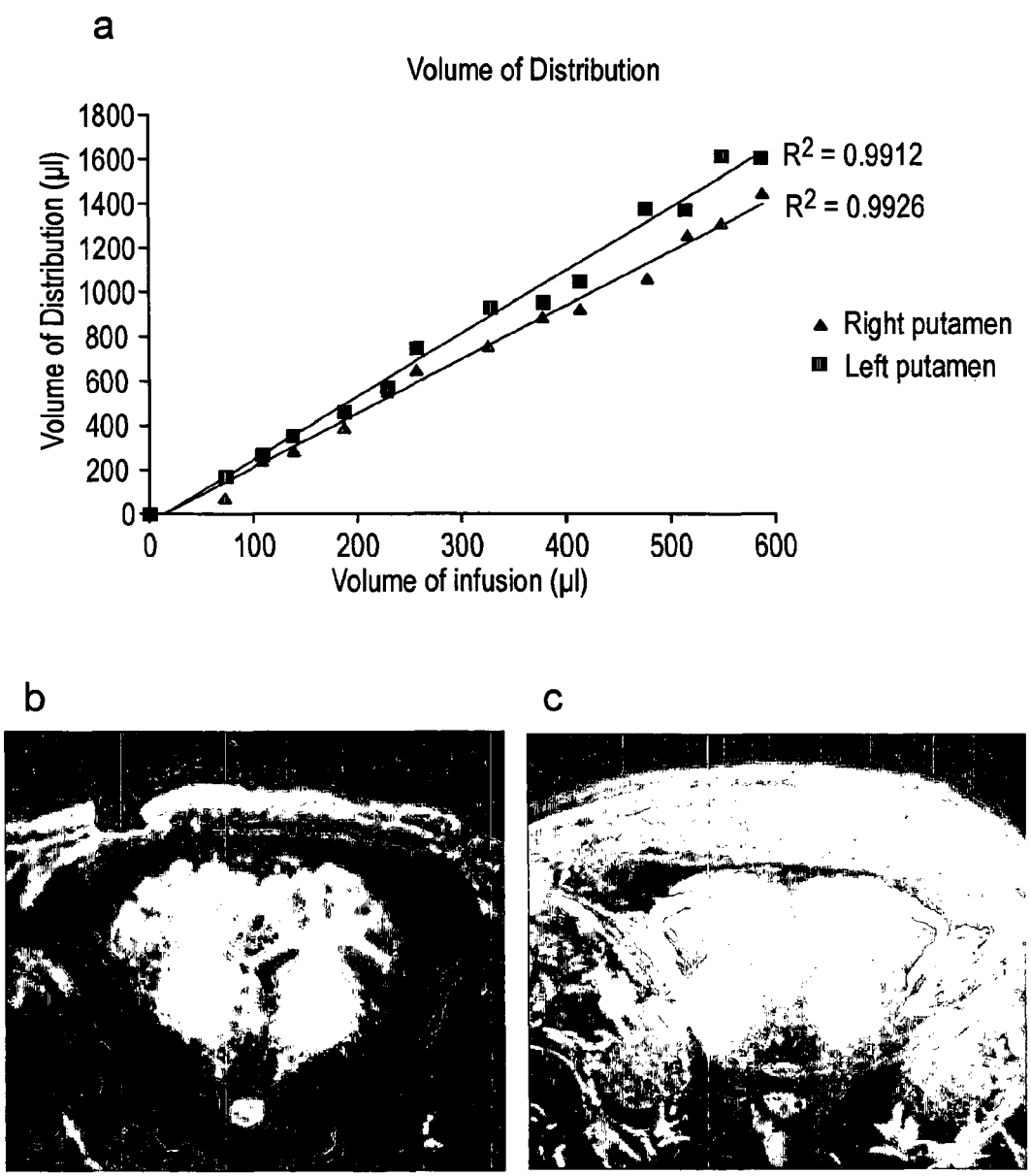
FIG. 11 shows (a) a graph of volume distribution versus volume of infusion for bilateral putamenal infusions of Gd-DTPA (0.25% in artificial CSF) in a pig using a recessed catheter (b) a 3D reconstruction of a MRI scan of the pigs brain after infusion and (c) a T1 weighted MR image of the pigs brain after infusion.
Figure 12:
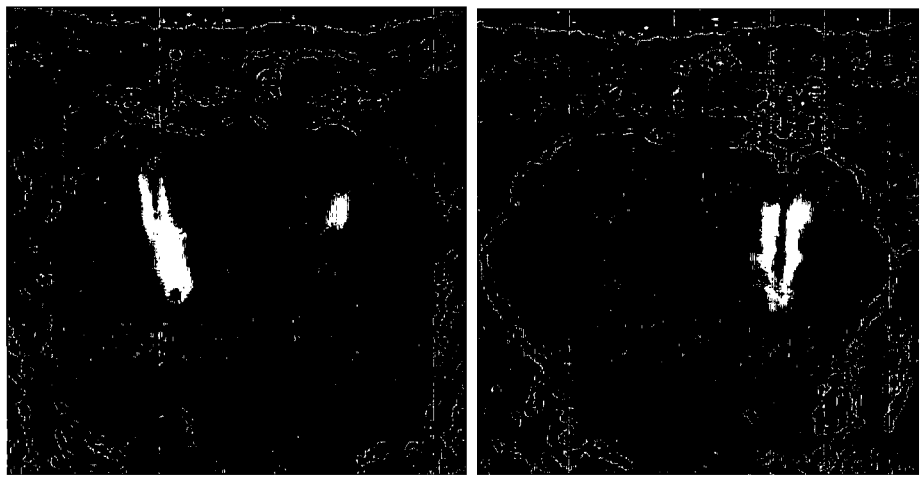
FIG. 12 shows images of reflux in a pigs brain infused with fluid using a stepped catheter implanted in the left had side (a) and in the right hand side (b)

As can be seen by comparing the images of FIG. 11 to FIG. 12, reflux has been dramatically reduced.

As shown by FIG. 10, when the step length was increased to 15 mm, a volume of 15,500 µl was infused without significant reflux, achieving a spherical volume of distribution of 24,000 mm$^3$, with a diameter of 36 mm.

This neurological apparatus has advantages over previously described stepped catheters not only in its improved reflux resistance but its material properties and delivery technique enable its safe application for multiple simultaneous infusions with the scalp closed and sub chronic use over days or weeks if required (skull fixation of catheters-ability to infuse contrast prior to infusing drug, with time for contrast clearance)

This is in contrast to previously described stepped cannulae such as Smart Flow and ERG valve tip catheters which are rigid cannulae that can only be applied when guided by a stereotactic frame mounted at the head therefore only one catheter can be inserted at a time with the scalp and burr hole open, increasing the risk of infection, brain shift, and risk to the patient as they are manoeuvred in and out of an MM scan with a stereotactic frame secured to the head (prolonged and risky procedure, therefore multiple infusions to fill large volumes is impractical, especially as planning has to be done before each infusion).

Neurological apparatus according to the invention may be used in oncology and the treatment of neurodegenerative disease.

Figure 13:
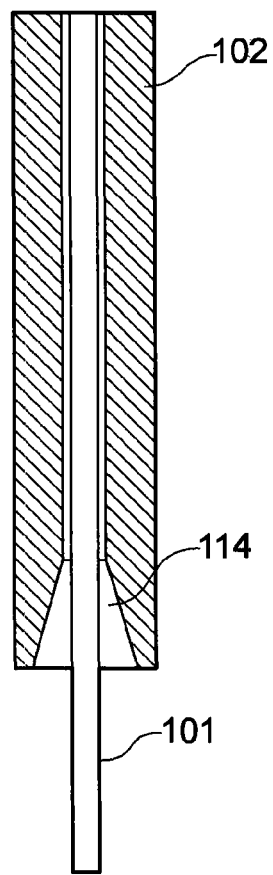
FIG. 13 shows a neurological apparatus according to another embodiment of the invention.

It will be understood that modifications and alterations can be made to the above-described embodiment without departing from the invention as defined in the claims. For example, rather than step between the tip 11 and flexible tubing 10, there may be a gradual increase in diameter from the distal section to the intermediate section of the catheter. Additionally, rather than the outer diameter of the catheter 1 changing in diameter, an internal diameter of the guide tube may change to provide a recess at the distal end. An example of such a catheter is shown in FIG. 13, where like reference numerals have been used for like parts but in the series 100. Specifically, the catheter 101, guide tube 102 and recess 114 are shown.

Preferably, a stop 3 is provided for limiting the extent to which the catheter 1 can be inserted into the guide tube 2. However, other indications identifying the length of the catheter to be inserted in the guide tube may be provided, such as an indicium on the catheter, which, when aligned at a specified location on the guide tube identifies that the port is located at the target site Rather than the catheter increasing in diameter from a distal section to an intermediate section a length of further tubing separate from the guide tube and catheter may be provided. The further tubing arranged, in use, to receive the catheter with the catheter extending through the entire length of the further tubing and to be received in the guide tube such that a distal end of the further tube is spaced from and contained within the guide tube to define the recess.

An example of such an arrangement is shown in FIGS. 14a to 14d. The catheter shown in FIGS. 1 to 6 is suitable for treatment of acute conditions wherein the catheter is only to be inserted into the patient for a short period of time. Treatments of the brain over longer periods of time, such as for chronic conditions, may be unsuitable using the catheter of FIG. 1 because the stiff tip 11 of the catheter can become blocked. Accordingly, to treat patients for longer periods a catheter that is more flexible along its length is required. In the embodiment shown in FIGS. 14a to 14d the distal end and the main body (not shown) of the catheter 33 is made of flexible material, in this embodiment carbothane. The catheter 33 is a single length of tubing having a constant diameter and is delivered through an intermediate tubing 31, which may also be made of carbothane, that is located in the guide tube 30 such that its end falls short of the end of the guide tube 30 in order to provide the recess 14.

Figure 14A:
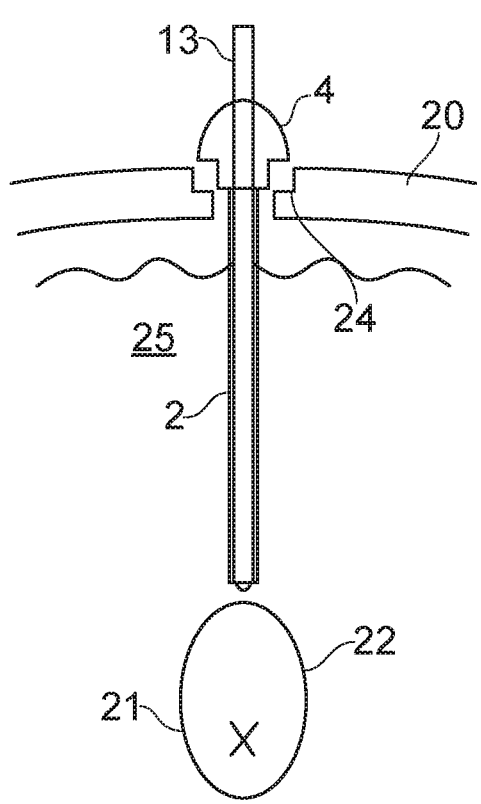
FIGS. 14a to 14d show schematically a method of inserting a neurological apparatus according to another embodiment of the invention into the brain.
Figure 14B:
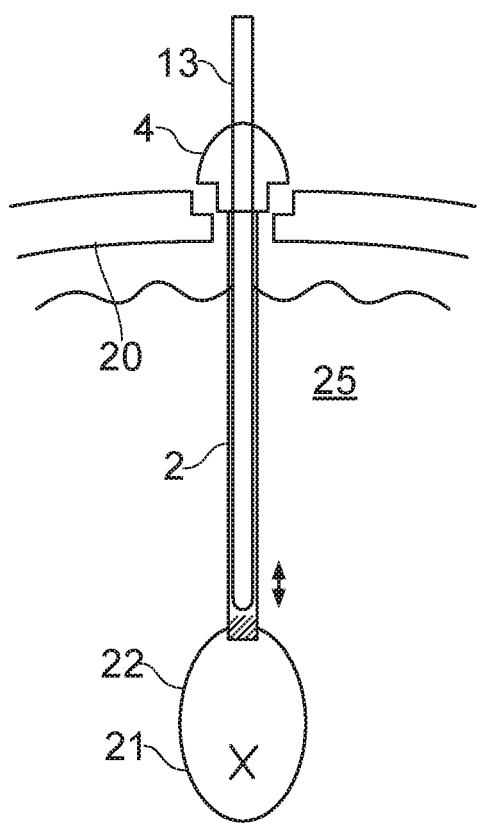

Because the tip of the catheter 33 is made of flexible material, to deliver the flexible tip to the target site a channel though the brain tissue is first formed using a stiffer rod or wire 30. After forming the channel, the stiff rod or wire 30 is removed and the flexible tip of the catheter 33 is then fed into the channel. FIGS. 14a and 14b show the steps of coring a plug of tissue using the guide tube and correspond to the steps shown in FIGS. 5a to 5c. However, FIG. 14c shows the step of forming a channel to the target site 21 before the flexible tipped catheter 33 is inserted in the channel, as shown in FIG. 14d.

Figure 14C:
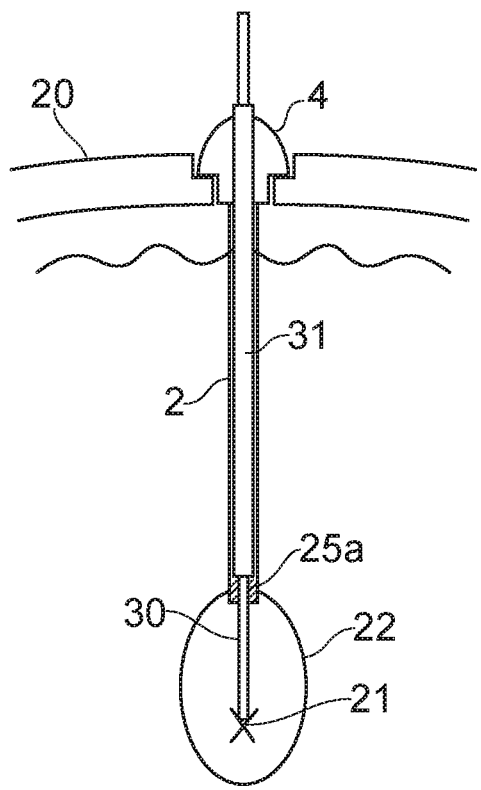
Figure 14D:
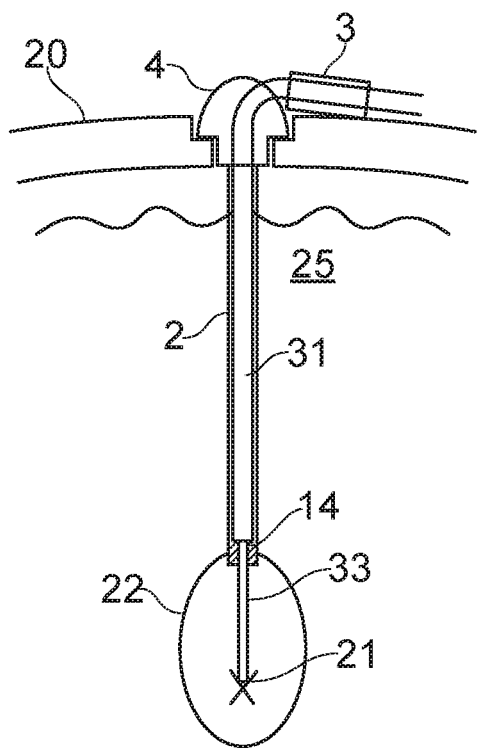

Describing the steps shown in FIGS. 14c and 14d in more detail, the stiff rod 30 is secured within the intermediate tube 31 such that the distal ends of the rod 30 and intermediate tube 31 are substantially coincident. This combination of the stiff rod 30 and intermediate tubing 31 is inserted into the guide tube 30 until the distal ends are located approximate the cored brain tissue 25a. The rod 30 is then unsecured from the intermediate tube 31 and lowered further into the brain, forming a channel through the brain tissue to the target, as shown in FIG. 14c. The rod 30 is then removed and a flexible catheter 33 inserted through the intermediate tube 31, which has remained in place in guide tube 2, into the channel and to the target site 21.

Initially, the seal formed between the catheter 33 and the cored brain tissue may not be as good as that formed when using a stiff tipped catheter 1. However, over time, healing of the brain tissue around the catheter tip will help to seal these regions against reflux.

In a further embodiment, separate tubing that surrounds the catheter may be inserted through the cored brain tissue together with the catheter. This may be useful, for example for forming a step between the recess and the target site. In such an embodiment, the recess may be formed between the tubing that surrounds the catheter and the guide tube. In such an embodiment, there may be two intermediate tubes, one that is passed through the cored brain tissue with the catheter and one whose distal end is located upstream of the cored brain tissue.

Sealing elements may be provided for sealing gaps between the tubes to prevent CSF or infusate that may pass through the gaps from leaking from the catheter system. In particular, the stop may comprise a tapering portion arranged to extend into and engage a section of the hub/intermediate tubing/guide tube to seal a gap between the hub/intermediate tube/guide tube and the catheter 1. Furthermore, in the embodiment wherein an intermediate tube is provided separate from the catheter, a separate o-ring may be located in the hub and the intermediate tubing may pass through the o-ring such that the o-ring seals a gap between the intermediate tubing and the guide tube.

An alternative possibility to having a series of catheters with different length tips 11 is to have a catheter with an adjustable tip length.

Rather than the surgeon selecting the catheter for a set of available catheters and fixing the stop 3 in position, a bespoke catheter may be manufactured specific to a surgeon's requirements, such as with the stop 3 fixed in position at a place specified by the surgeon and with a specified length of tip 11. The bespoke catheter may be ordered by the surgeon before implanting the guide tube or after the guide tube has been implanted and an image obtained of the patient's brain with the guide tube implanted.

The invention claimed is:

1. A neurological kit comprising:
   a guide tube;
   an intermediate tube including a distalmost end and an insertion length configured to be inserted into the guide tube; and
   a catheter, the catheter including a distal section of tubing having a distal end with a port for delivering fluid to a target site within the brain, wherein:
   the insertion length is shorter than the guide tube such that when the intermediate tube is positioned at a final position, the insertion length is fully contained within the guide tube and the distalmost end of the intermediate tube and a distal section of the guide tube form a recess in the guide tube, the recess having an open distal end and a closed proximal end formed by the distalmost end of the intermediate tube fully contained within the guide tube; and
   the catheter is configured to be inserted into and moves axially relative to the intermediate tube when the intermediate tube is located in the guide tube, and the catheter is configured to pass through the recess to locate the port at the target site.

2. A neurological kit according to claim 1, wherein the recess is dimensioned to retain a volume of brain tissue sufficient to act as a seal against reflux along the guide tube of fluid delivered using the catheter.

3. A neurological kit according to claim 1, wherein the recess extends at least 0.5 mm into the guide tube.

4. A neurological kit according to claim 3 wherein the recess extends about 3 mm into the guide tube.

5. A neurological kit according to claim 1, wherein the intermediate tube has an outer diameter greater than the outer diameter of the distal section of the catheter that defines the recess and an internal diameter less than the internal diameter of the guide tube that defines the recess, and the intermediate tube is located or locatable in the guide tube with a distal end of the length of tubing spaced from a distal end of the guide tube.

6. A neurological catheter according to claim 5, wherein an internal diameter of the guide tube decreases between a distal end section and an intermediate section.

7. A neurological kit according to claim 6, wherein the decrease in internal diameter is a step between the intermediate section and the distal end section of the guide tube.

8. A neurological kit according to claim 6, wherein the decrease in diameter is a gradual decrease from a distal end section to the intermediate section of the guide tube.

9. A neurological kit according to claim 1, wherein the distal section of the catheter comprises a stiff, non-porous tip.

10. The neurological kit as claimed in claim 1, further comprising a winged stop provided on the catheter, the winged stop including a central tubular section and two wings.

11. A neurological device comprising:
a guide tube;
an intermediate tube including a distalmost end and an insertion length configured to be inserted into the guide tube; and
a catheter that includes a distal section of tubing having a distal end with a port or ports for delivering fluid to a target site within a brain, wherein:
the catheter is received in the guide tube such that the port or ports are located at the target site in the brain;
the insertion length is shorter than the guide tube such that the insertion length is fully contained within the guide tube, and the distalmost end of the intermediate tube and a distal section of the guide tube form a recess in the guide tube, the recess having an open distal end and a closed proximal end formed by the distalmost end of the intermediate fully contained within the guide tube; and
the catheter is configured to move axially relative to the intermediate tube and pass through the recess to locate the port at the target site.

12. A neurological device according to claim 11, wherein the recess is configured to contain compressed brain tissue.

13. A neurological kit comprising:
a guide tube that can be cut to a required length;
a catheter comprising a distal section of tubing having a distal end with a port or ports for delivering fluid to a target site within the brain, the distal section of tubing including an outer diameter that is smaller than an internal diameter of the guide tube;
an intermediate tube comprising an insertion length configured to be inserted into the guide tube, wherein:
the insertion length is shorter than the guide tube such that upon full insertion of the insertion length into the guide tube, the distalmost end of the intermediate tube and a distal section of the guide tube form a recess in the guide tube, the recess having an open distal end and a closed proximal end formed by the distalmost end of the intermediate tube housed within the guide tube; and
the catheter is configured to be inserted into and moves axially relative to the intermediate tube when the intermediate tube is located in the guide tube, and the catheter is configured to pass through the recess to locate the port at the target site.

14. A neurological kit comprising:
a guide rod;
a guide tube, the guide tube being provided over the guide rod such that a combination of the guide rod and the guide tube for insertion into a brain comprises a longitudinal axis;
a stop located at an end portion of the guide tube;
an intermediate tube that includes a distalmost end and an insertion length configured to be inserted into the guide tube; and
a catheter, wherein:
the stop is configured to restrict movement of the combination such that the combination stops short of full insertion of the guide tube to a final location while being configured to allow movement of the guide tube relative to the guide rod along the longitudinal axis to a final location in the brain;
the guide rod being configured to be withdrawn from the guide tube while the tube is positioned in the final location;
the insertion length is shorter than the guide tube such that when the insertion length of the intermediate tube is wholly inserted into the guide tube, a recess is formed in the guide tube, the recess having an open distal end and a closed proximal end formed by the distalmost end of the intermediate tube housed within the guide tube.

15. A neurological kit according to claim 14, wherein the guide tube comprises a hub that includes the stop such that a proximal end of the guide tube comprises a narrowing profile for abutting a hole in a skull to define the final location of the guide tube in the brain.

16. A neurological kit according to claim 15, wherein the narrowing profile is a stepped profile.

* * * * *